US00PP32082P3

(12) United States Plant Patent
Lovengreen Ferreira

(10) Patent No.: US PP32,082 P3
(45) Date of Patent: Aug. 18, 2020

(54) ***ARISTOTELIA* PLANT NAMED 'VB1'**

(50) Latin Name: *Aristotelia chilensis*
Varietal Denomination: VB1

(71) Applicant: Royal Super Fruits B.V., Katwijk aan Zee (NL)

(72) Inventor: Axel Lovengreen Ferreira, Pitrufquen (CL)

(73) Assignee: ROYAL SUPER FRUITS B.V., Katwijk Aan Zee (NZ)

( * ) Notice: Subject to any disclaimer, the term of this patent is extended or adjusted under 35 U.S.C. 154(b) by 0 days.

(21) Appl. No.: 16/602,064

(22) Filed: Jul. 29, 2019

(65) Prior Publication Data

US 2020/0045865 P1 Feb. 6, 2020

(30) Foreign Application Priority Data

Jul. 31, 2018 (QZ) ..... PBR 2018/1996

(51) Int. Cl.
*A01H 5/00* (2018.01)
*A01H 6/00* (2018.01)
*A01H 5/12* (2018.01)

(52) U.S. Cl.
USPC ..... Plt./216
CPC ..... *A01H 6/00* (2018.05); *A01H 5/12* (2013.01)

(58) Field of Classification Search
USPC ..... Plt./216
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Aristotelia chilensis* plant named 'VB1' that is characterized by its vigorous evergreen growth habit and its slightly glossy leaves that are dark green in color.

2 Drawing Sheets

Botanical classification: *Aristotelia chilensis*.
Varietal denomination: 'VB1'.

CROSS REFERENCE TO RELATED APPLICATIONS

This application is co-pending with a U.S. Plant Patent Applications filed for a plant derived from the same breeding program that are entitled *Aristotelia* Plant Named 'Pretoria' (U.S. Plant patent application Ser. No. 16/602,063), *Aristotelia* Plant Named 'Sobresale' (U.S. Plant patent Ser. No. 16/602,062), and *Aristotelia* Plant Named 'AZ50' (U.S. Plant patent Ser. No. 16/602,061).

BACKGROUND OF THE INVENTION

The present invention relates to a new and distinct cultivar of *Aristotelia chilensis* and will be referred to hereafter by its cultivar name, 'VB1'. 'VB1' represents a perennial evergreen shrub grown for landscape plant.

'VB1' was discovered by the Inventor as a chance seedling in a field garden in Pitrufquen, IX region de la Araucanía, Chile in January of 2017. The field had been planted with numerous unnamed proprietary seedling plants from the Inventor's breeding program. The parentage is therefore unknown.

Asexual propagation of the new cultivar was first accomplished by softwood stem cuttings by the Inventor in summer of 2017 in Pitrufquen, IX region de la Araucanía, Chile. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'VB1' as a unique cultivar of *Aristotelia chilensis*.

1. 'VB1' exhibits a vigorous evergreen growth habit.
2. 'VB1' exhibits slightly glossy leaves that are dark green in color.

'VB1' can be most closely compared to the *Aristotelia chilensis* cultivars 'Variegata' (not patented), 'Pretoria', 'Sobresale', and 'AZ50'. 'Variegata' differs from 'VB1' in having foliage that is variegated and a narrower and less open plant habit. 'Pretoria' differs from 'VB1' in having green branches, green young foliage and mature foliage that is blue-green in color. 'AZ50' differs from 'VB1' in having a more open plant habit, a wider plant shape, branches that are more green in color, young leaves that are more yellow-green in color and mature foliage that is less blue-green in color and less glossy. 'Sobresale' differs from 'VB1' in having green branches, less glossy foliage and lighter and less yellow-green mature foliage.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new

*Aristotelia.* The photographs were taken of a 24-month-old plant (with a single prune 3 weeks prior) of 'VB1' as grown in a greenhouse in a 30-cm container in Boskoop, The Netherlands.

Figure 1:
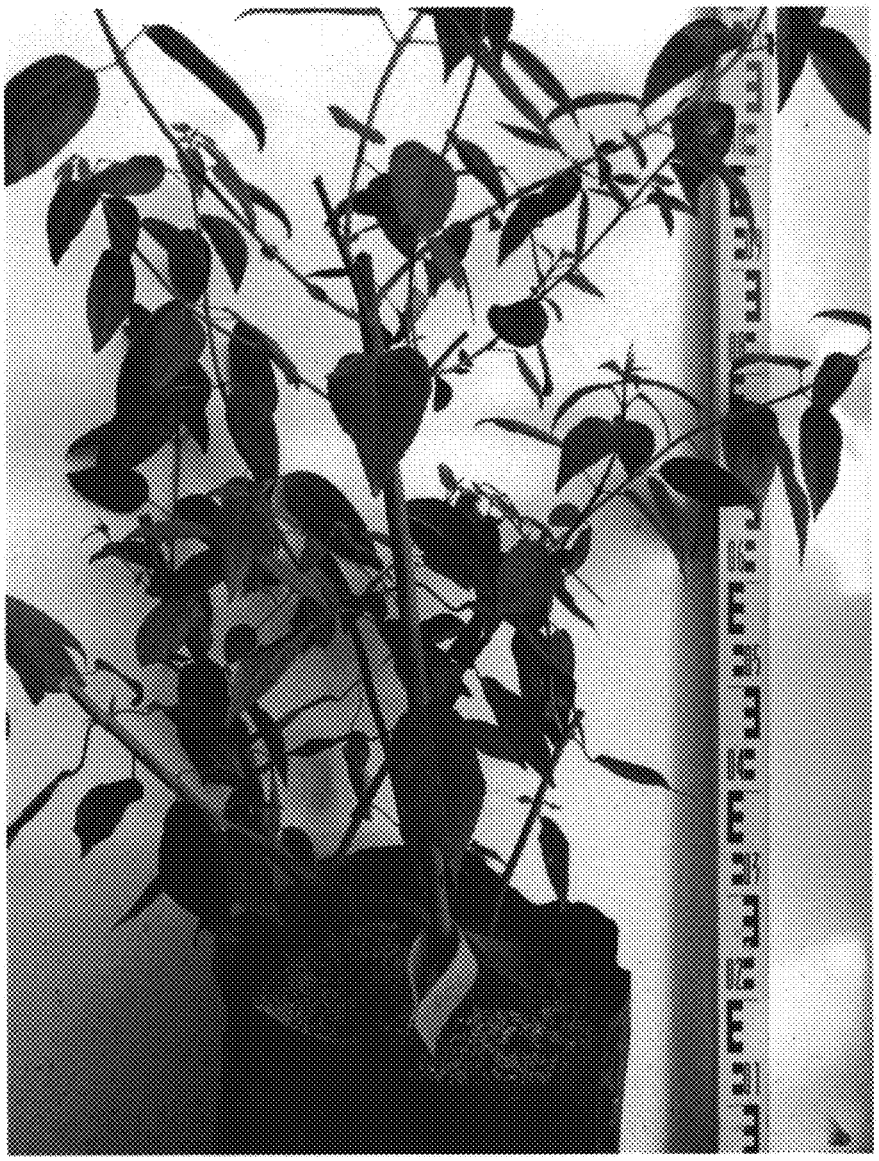

The photograph in FIG. 1 provides a view of the plant habit of 'VB1'.

Figure 2:
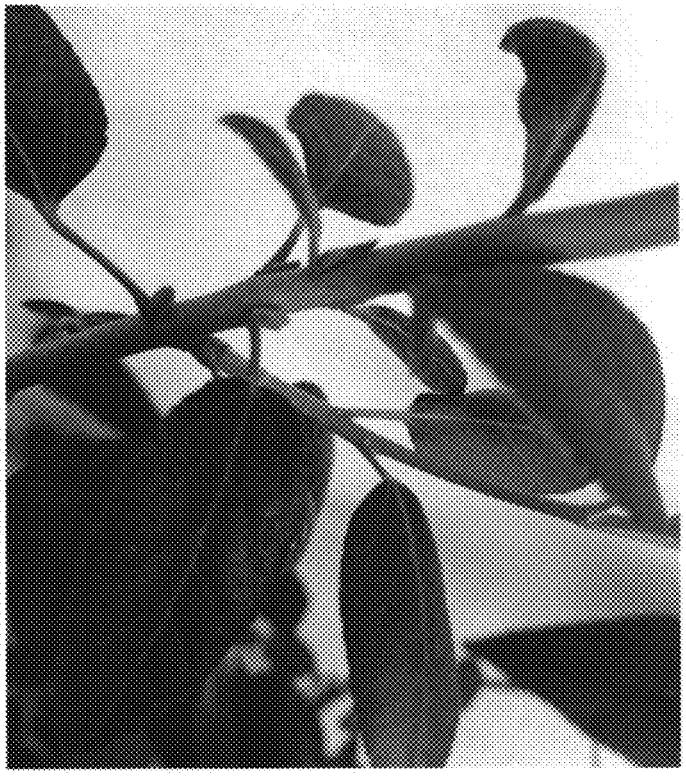

The photograph in FIG. 2 provides a close-up view of the young foliage of 'VB1'.

Figure 3:
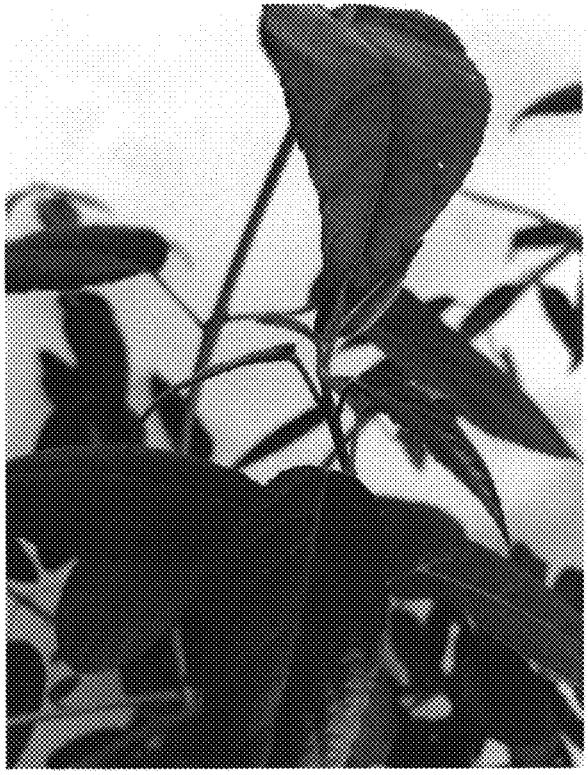

The photograph in FIG. 3 provides a close-up view of the mature foliage of 'VB1'.

The colors in the photographs are as close as possible with the photographic and printing technology utilized and the color values cited in the detailed botanical description accurately describe the colors of the new *Aristotelia.*

BOTANICAL DESCRIPTION OF THE PLANT

The following is a detailed description of 24-month-old plants (with a single prune 3 weeks prior) of 'VB1' as grown in a greenhouse in 30-cm containers in Noordwijkerhout, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Perennial, evergreen shrub.

*Plant habit.*—Broadly obovate.

*Height and spread.*—An average of 89 cm in in height and 105.5 cm in spread, reaches 2.9 m in height and 2.5 m in spread as a mature plant in the landscape.

*Cold hardiness.*—At least in U.S.D.A. Zone 8.

*Diseases and pests.*—No susceptibility and resistance to diseases or pests has been observed.

*Root description.*—Fine and fibrous.

*Propagation.*—Softwood stem cuttings.

*Root development.*—An average of 60 days for root initiation with a young rooted plant produced in an average of 4 months.

*Growth rate and vigor.*—Moderate.

Stem description:

*Stem shape.*—Rounded.

*Stem strength.*—Strong.

*Stem color.*—Young; 144A, mature; 152B, tinged 176A, internodes; 152B, tinged 176A, old bark; a color between 137B and 138A.

*Stem size.*—An average of 23.9 cm in length and 3 mm in diameter.

*Stem surface.*—Young and mature; Moderately glossy and covered with a very thin wax layer, 188A in color, old bark; densely covered with lenticels; an average of 1.5 mm in length, 1 mm in width and 157A in color.

*Stem aspect.*—Average angle of vertical to 40°.

*Internode length.*—An average of 3.3 cm.

*Branching.*—Freely branching with an average of 1 main branch and 42 lateral branches.

Foliage description:

*Leaf shape.*—Narrow ovate.

*Leaf arrangement.*—Opposite to near opposite to alternate.

*Leaf aspect.*—Moderately to moderately undulate.

*Leaf division.*—Simple.

*Leaf base.*—Acute.

*Leaf apex.*—Acute to bluntly acute.

*Leaf margins.*—Serrate.

*Leaf venation.*—Pinnate, color; upper surface 148A, tinged 177B to 177C, lower surface 145C.

*Leaf size.*—An average of 13.2 cm in length and 5.8 cm in width.

*Leaf attachment.*—Petiolate.

*Leaf number.*—An average of 16 (8 pairs).

*Leaf surface.*—Upper surface; moderately glossy and glabrous and slightly rugose, lower surface; smooth, glabrous and slightly rugose with small tufts on the vein axils.

*Leaf color.*—Young foliage; upper surface 146A to 146B, young lower surface 146A, changing to 152A to 152B at the margins, mature foliage; upper surface between 147A and N189A and covered with a very thin waxy layer 188A, mature lower surface NN137C to NN137D.

*Petioles.*—An average of 3.3 cm in length and 1.75 mm in diameter, strong, upper surface color 178A, lower surface color 145A and moderately tinged with 178B, upper surface slightly glossy, lower surface matte and smooth and moderately pubescent with hairs an average of 0.3 mm in length and too small to measure color.

Inflorescence description: No flower production produced to date on plants available for data collection.

Fruit and seed: No production observed to date on plants available for data collection.

It is claimed:

1. A new and distinct cultivar of *Aristotelia* plant named 'VB1' substantially as herein illustrated and described.

* * * * *